United States Patent [19]

Collins

[11] Plant 4,756

[45] Aug. 4, 1981

[54] WHITE ASH

[75] Inventor: William H. Collins, Circleville, Ohio

[73] Assignee: American Garden Cole, Inc., Circleville, Ohio

[21] Appl. No.: 140,012

[22] Filed: Apr. 14, 1980

[51] Int. Cl.[3] ..... A01H 5/12

[52] U.S. Cl. ..... Plt./51

[58] Field of Search ..... Plt./51

*Primary Examiner*—Robert E. Bagwill

*Attorney, Agent, or Firm*—Maky, Renner, Otto & Boisselle

[57] ABSTRACT

A new and distinct variety of white ash tree, characterized by a strong, sturdy, upright branching habit which forms a compact, oval to globe-shaped head.

3 Drawing Figures

1

My present invention or discovery relates to a new and distinct variety of white ash originated by me, having unusual and distinctive characteristics, and more particularly consists in a white ash, *Fraxinus americana,* having a novel habit of growth.

This new variety of white ash tree is distinguished from other white ash trees by its strong, sturdy, upright branches which form a compact, oval to globe-shaped head. Such an upright growth habit, evidenced by branches which grow in a uniform, upright manner, is in striking contrast to the wider spreading branching habit characteristic of the species. This makes such new variety of white ash an ideal landscape specimen for street, park or residential planting where an up-right tree is desired, in that there is no need to remove lower branches once height of head is established, whereby very little maintenance is required.

The original specimen originated as a seedling selected by me from a block of white ash seedlings made by me. My new white ash tree has been propagated asexually at Circleville, Ohio, by budding, and I have found that the above-indicated desirable characteristics are consistently perpetuated in the progeny. Budded trees of this new variety are now growing at Circleville, Ohio, and demonstrate the same novel characteristics.

Referring now more particularly to the drawing.

Figure 1:
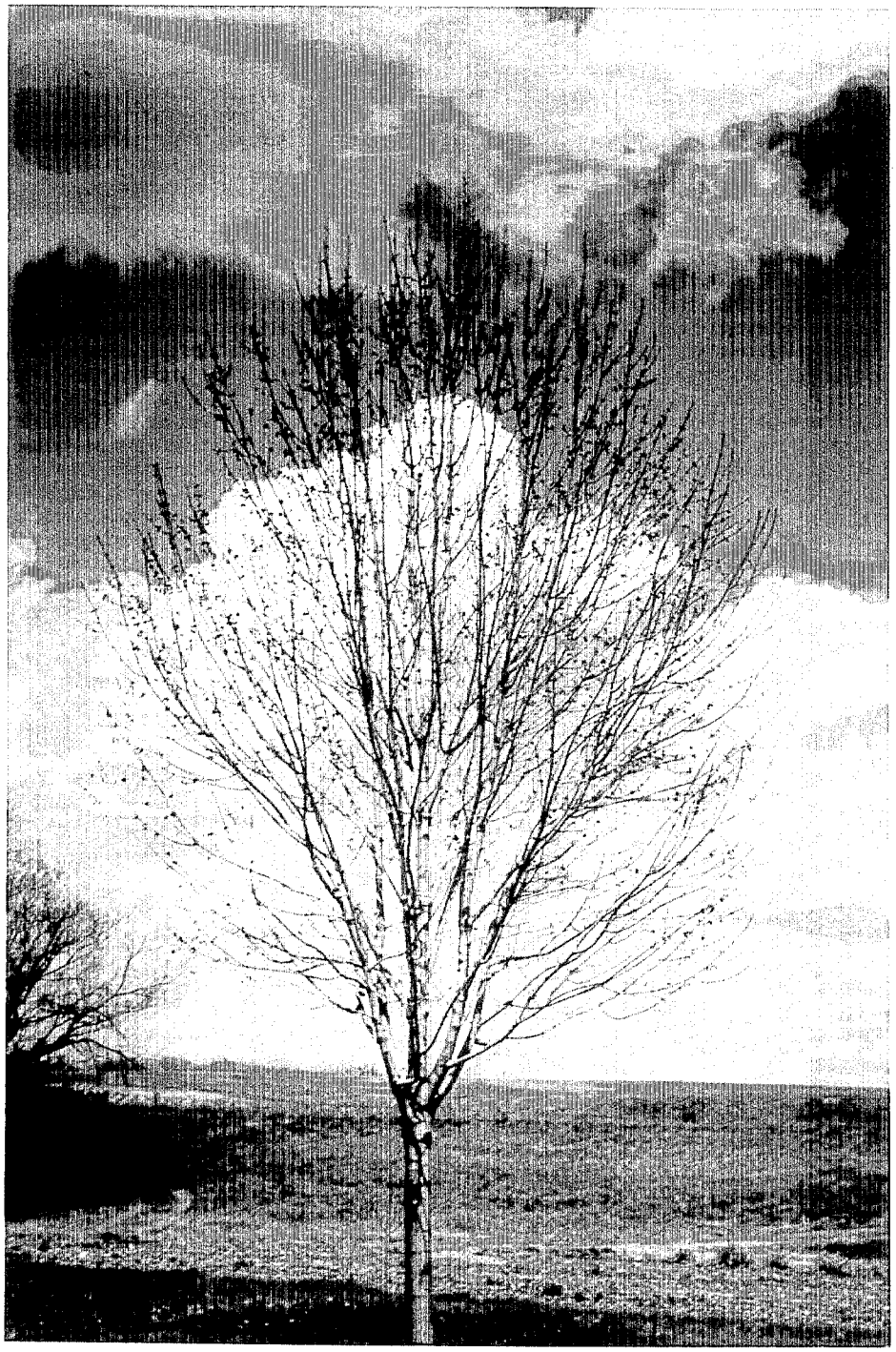
FIG. 1 shows my new white ash tree in winter after dropping of the foliage showing its uniform upright habit.
Figure 2:
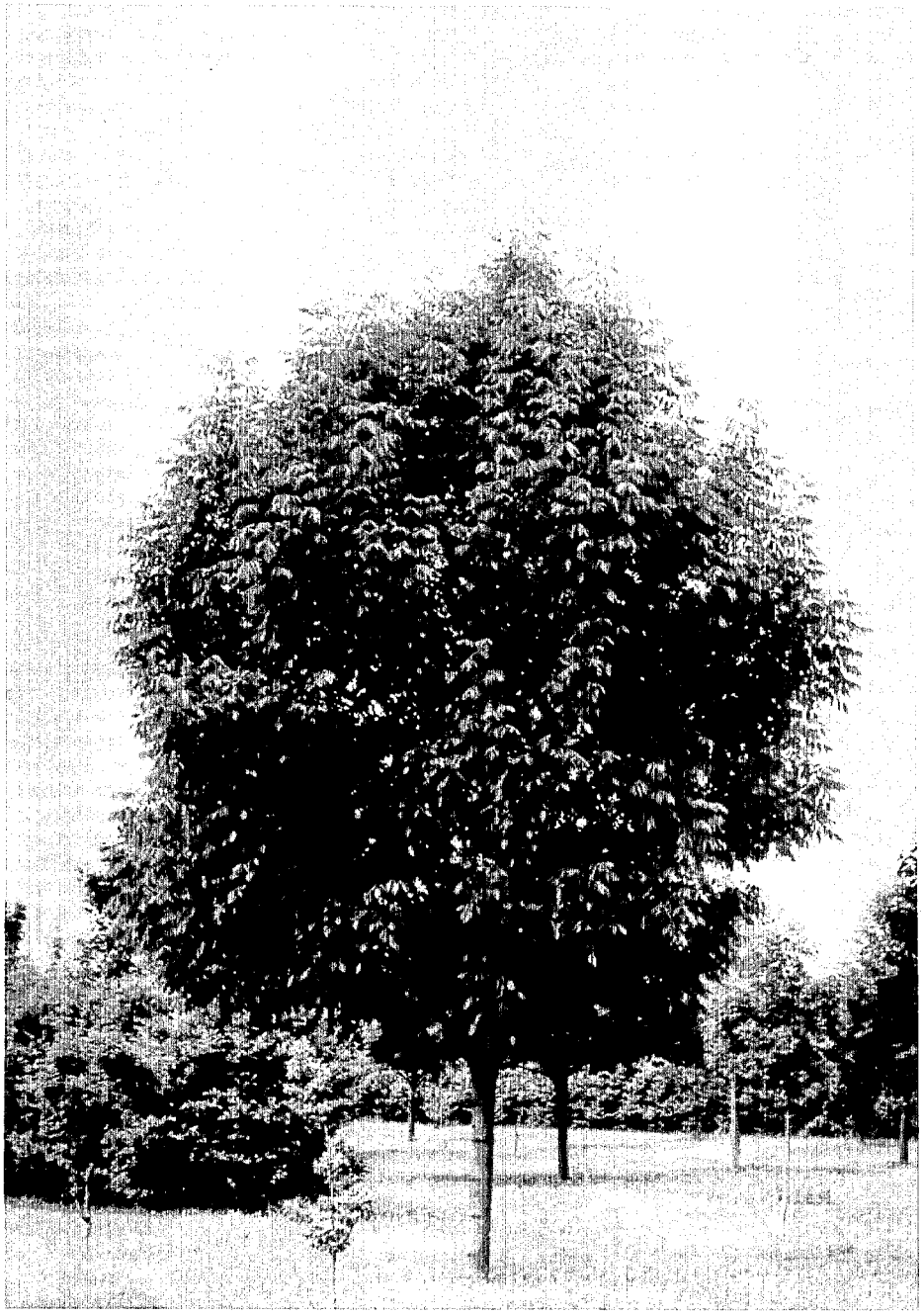
FIG. 2 shows such tree in full summer foliage.
Figure 3:
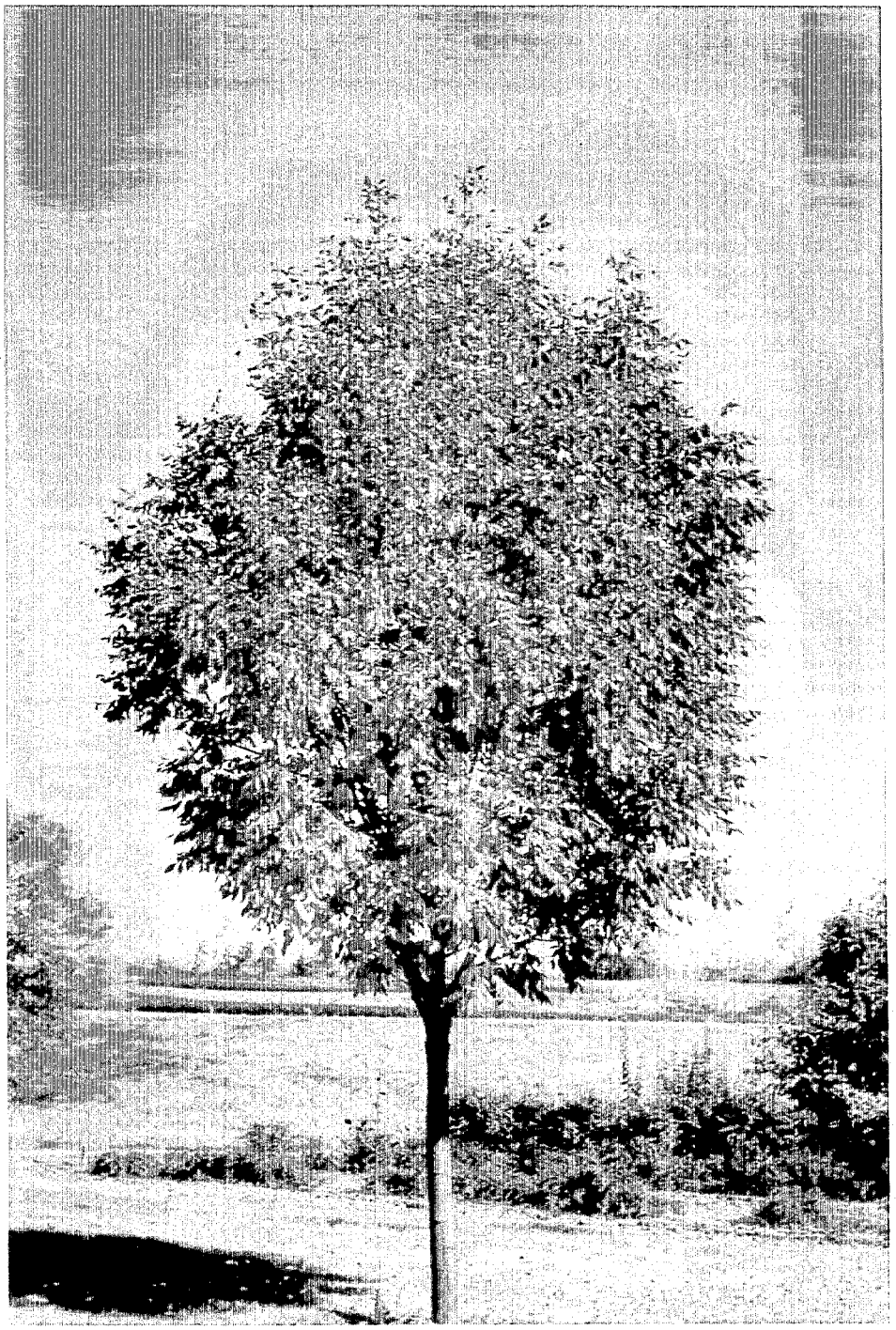
FIG. 3 shows such tree in full fall color.

The original specimen on the premises of American Garden Cole, Inc., in Circleville, Ohio, at 15 years of age, was approximately 25 feet in height, with an oval to globe-shaped head, approximately 12 to 14 feet in width, formed by stout, upright branches, extending from the main trunk at approximately 45° angles.

The growth rate of this new variety is somewhat slower than that of the species. The 15 year old original specimen measured 8 inches in trunk diameter at 4½ feet above ground. The terminal twig growth for 1978 measured from 12 to 15 inches in length, but was somewhat slower in 1977 and 1976.

2

The branchlets are of a stout texture, glabrous, terete as is typical of the species. The color of the branchlets is moderately olive green to grayish brown, often tinged with purple. The color varies with age of the branchlets. Lenticels are sparing to semi-prominent.

The terminal buds are brown, small, coming to a rounded point, slightly hairy and usually with 4 scales. The side buds are opposite, small and rounded. The first side bud is set directly below the terminal, and sunken into the leaf scar. Bundle scars are prominent.

The leaves and leaflets do not differ greatly from those of the species. The leaves are 6½ to 8 inches long, pinnately compound. Leaves are composed of 5 to 9 opposite leaflets, usually with a terminal leaflet. The leaflets are dark green, glabrous above, light green to glaucous beneath, glabrous to slightly hairy. Leaflets have 10 to 12 pairs of veins with a glabrous or slightly hairy midrib. Leaflets vary in size, depending on the growth rate of the twigs, from 6.0 to 14.0 cm. long and 2.5 to 6 cm. wide. Leaflets are oval to elliptic lanceolate in shape, accuminate at the tip and slightly cuneate at the base. The leaf rachis is terete and usually purplish in color. Leaflet stalks are 5 to 20 mm. in length. In the fall the leaves take on an attractive, deep, bronzy purple to orange red color.

Flowers, appearing in late April, appear to be all male as no fruit has been observed to develop on the original specimen or on any of the progeny. Anther stems and pollen sacks are purplish green in color.

Because of its unusual upright branching habit, my new variety of white ash tree is particularly suited for street, park or residential landscape planting.

I claim:

1. A new and distinct variety of white ash tree, *Fraxinus americana,* substantially as described and illustrated, characterized by a strong, sturdy, upright branching habit which forms a compact, oval to globe-shaped head.

* * * * *